(12) United States Patent
Dixon et al.

(10) Patent No.: US 10,117,859 B2
(45) Date of Patent: Nov. 6, 2018

(54) DOSAGE SUSPENSIONS OF ACTIVE PHARMACEUTICAL INGREDIENTS

(71) Applicant: Southwest Research Institute, San Antonio, TX (US)

(72) Inventors: Hong Dixon, Helotes, TX (US); Larry A. Cabell, San Antonio, TX (US); Joseph A. McDonough, Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 15/193,254

(22) Filed: Jun. 27, 2016

(65) Prior Publication Data

US 2017/0368042 A1    Dec. 28, 2017

(51) Int. Cl.
*A61K 31/444* (2006.01)
*A61K 31/5375* (2006.01)
*A61K 31/439* (2006.01)

(52) U.S. Cl.
CPC .......... *A61K 31/444* (2013.01); *A61K 31/439* (2013.01); *A61K 31/5375* (2013.01)

(58) Field of Classification Search
CPC ...... A61K 9/10; A61K 31/439; A61K 31/444; A61K 31/5375
See application file for complete search history.

(56) References Cited

U.S. PATENT DOCUMENTS

| | | | |
|---|---|---|---|
| 8,404,850 B2 | 3/2013 | Cabell et al. | |
| 8,722,706 B2 | 5/2014 | Dixon et al. | |
| 8,946,200 B2 | 2/2015 | McDonough et al. | |
| 2009/0281144 A1 | 11/2009 | Cabell et al. | |
| 2013/0183263 A1* | 7/2013 | Hoffman | A61K 38/12 424/78.32 |

FOREIGN PATENT DOCUMENTS

WO    2011008674 A1    1/2011

OTHER PUBLICATIONS

Santovena, A., et al "Study of Quality and Stability of Ursodeoxycholic Acid Formulations for Oral Pediatric Administration", International Journal of Pharmaceutics 477 (2014) pp. 32-38.

* cited by examiner

*Primary Examiner* — Michael B. Pallay
(74) *Attorney, Agent, or Firm* — Tucker Grossman (57) ABSTRACT

Methods for preparing suspensions of active pharmaceutical ingredients for ensuing drug delivery. The suspension may include a mixture of a relatively low dosage API and a relatively high dosage API or a mixture of an API with a suitable excipient.

11 Claims, 6 Drawing Sheets

DOSAGE SUSPENSIONS OF ACTIVE PHARMACEUTICAL INGREDIENTS

GOVERNMENT SUPPORT CLAUSE

This invention was made with United States Government support under Contract No. W911QY1310001 from the Department of the Army. The Government has certain rights in this invention.

FIELD OF THE INVENTION

The present disclosure relates to preparation of dosage suspensions of active pharmaceutical ingredients (API). More specifically, the suspensions include a mixture of a relatively low dosage API and a relatively high dosage API or a mixture of an API and a suitable excipient.

BACKGROUND

Pharmaceutical are the most commonly employed method to deliver drug substances. However, a difficulty in the formulation and preparation of relatively low dose active pharmaceutical ingredients is content uniformity. At low dosages, relatively good content uniformity of a mixture of one API (targeted for relatively low dosage) and one API (targeted for a relatively higher relative dosage) is challenging. Similarly, at low dosages, relatively good content uniformity of a mixture of one API (targeted for relatively low dosage) with an excipient (present at a relatively high level), is again difficult to achieve in connection of assuring reliable drug uniformity.

For example, when two APIs are to be delivered in suspension, where one is targeted at a relatively low dosage, and one is targeted for a relatively high dosage, separate milling of the solid APIs, and then combination of the two APIs, typically leads to difficulty in measurement and non-uniformity in suspension content, thereby raising concerns that dosage targets have been compromised.

In fact, it is particularly challenging to deliver a relatively low dose medicine from a suspension dosage when dealing with relatively small volume (as low as 0.1 mL) of a relatively low concentration formulation (e.g., 0.5% or less). For example, it has been reported that the average content uniformity of delivering a 5.0 mL volume of a 1.5% suspension formulation could vary as much as 47% to 108%. See, A. Santoven, E, Sanchez-Negrin, L Charola, M. Llabres, J. G. Farina, "Study of Quality and Stability of Ursodeoxyvholic Acid Formulations for Oral Pediatric Administration, International Journal of Pharmaceutics 477 (2014) 32-38.

Attention is also directed to PCT/US2010/041665 entitled "Material And Process For Incorporation of Low Dosage Active Pharmaceutical Ingredients And Use Thereof." Disclosed therein is low dose API pharmaceutical tablet formed by spray coating a support excipient with the API. The resulting composition is described as being suitable for direct compression tablet formulation without the need for an additional granulation step to uniformly coat the API onto the support excipient. The support excipient comprises microcrystalline cellulose, a binder and a disintegrant, and is formed by spraying a homogenous slurry of the support excipient components.

Accordingly, the present disclosure is directed at a new method to ensure delivery with acceptable content uniformity for a drug suspension formulation containing a relatively low dose API and relatively high dose API, or a drug suspension formulation containing an API with an excipient.

SUMMARY

A method for forming a drug suspension comprising: (a) providing a first active pharmaceutical ingredient (API-1) targeted for relatively low dosage in the drug suspension; (b) providing a second active pharmaceutical ingredient (API-2) targeted for relatively high dosage in the drug suspension; (c) co-dissolving API-1 and API-2 in a common solvent; (d) removing the solvent and recovering a mixture of API-1 and API-2; (e) forming the drug suspension of the mixture of API-1 and API-2 in a liquid carrier wherein API-1 is present at a relatively low dosage and API-2 is present at a relatively high dosage.

A method for forming a drug suspension comprising: (a) providing a first active pharmaceutical ingredient (API-1) targeted for use in the drug suspension; (b) providing an excipient targeted for use in the drug suspension; (c) co-dissolving said API-1 and excipient in a common solvent; (d) removing the solvent and recovering a mixture of API-1 and the excipient; (e) forming the drug suspension of the recovered mixture of API-1 and the excipient in a liquid carrier wherein API-1 is present at a concentration of 0.1 mg/mL to 10.0 mg/mL.

A drug suspension composition comprising a first active pharmaceutical ingredient (API-1) at a relatively low dosage in vegetable oil and a second pharmaceutical ingredient (API-2) are relatively high dosage in said vegetable oil, wherein said API-1 and API-2 remain at a level of at least 60% of their original concentration after a period of 12 months at 60° C.

DETAILED DESCRIPTION

Provided herein is a method and drug suspension that uniquely facilitates the ability to more accurately and reliably provide, in suspension form, delivery of a relatively low dosage active pharmaceutical ingredient, in the presence of a relatively high dosage active pharmaceutical ingredient and/or an excipient.

Figure 1:
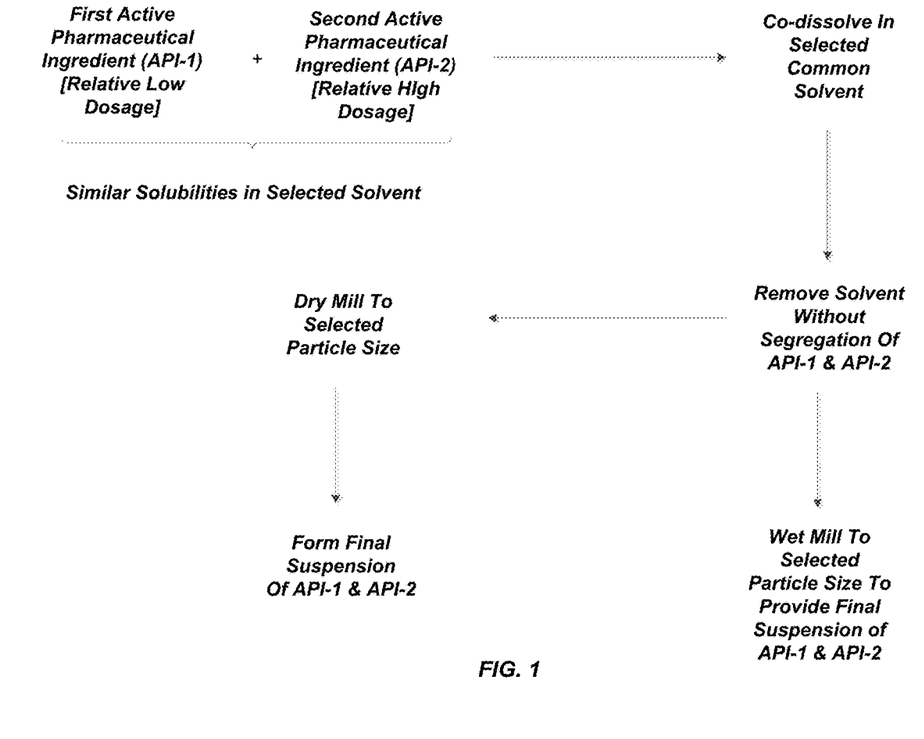
FIG. 1 illustrates the formation of a suspension of two active pharmaceutical ingredients where a first active pharmaceutical ingredient (API-1) is present at relatively low dosage and a second active pharmaceutical ingredient (API-2) is present at a relatively high dosage.

Attention is initially directed to FIG. 1 which illustrates the preferred methodology herein for preparation of a drug suspension containing the indicated active pharmaceutical ingredients. More specifically, a first active pharmaceutical ingredient (API-1) is selected that is targeted for relatively low dosage in the final drug suspension (e.g. in the range of 0.1 mg/mL to 10.0 mg/mL), and a second active pharmaceutical ingredient is selected (API-2) that is targeted for relatively high dosage in the final drug suspension (e.g. in the range of 20.0 mg/mL to 800.0 mg/mL).

API-1 and API-2 are then co-dissolved in a selected common solvent. API-1 and API-2 are preferably introduced into the common solvent at a weight ratio of 1:2 to 1:8000. Preferably, API-1 and API-2 have similar solubility is the selected common solvent. Similar solubility is understood herein to mean that with respect to the weight percent of API-1 and API-2 that co-dissolve in the common solvent, such respective weight percents of dissolution are within plus or minus 10% of one another. By way of example, if API-1 dissolves in the common solvent at a level of 90% by weight, then API-2 will preferably dissolve at the same level of 90% by weight. However, in the broad context of the present disclosure, it should be understood that that API-2 can dissolve at a level at low as 80% by weight to 100% by weight in the selected common solvent medium. In addition, and by way of additional example, if API-2 is such that it dissolves in the selected common solvent at a level of 90% by weight, then API-1 preferably dissolves in the selected common solvent at 90% by weight, or at a level of 80% by weight to 100% by weight.

Accordingly, the common solvent described herein may be any common solvent that provides the indicated solubility requirements. Such solvents may preferably include water miscible solvents and or water immiscible solvents. The solvents herein may therefore preferably include water, ethanol, isopropanol, acetone, and ethyl acetate.

Continuing, the two APIs dissolved in the common solvent are then next preferably removed from the solvent without segregation. Such removal from the solvent may preferably be achieved by one or more of lyophilisation (freeze drying), evaporation or spray drying. Accordingly, lyophilisation is reference to the procedure of freezing the solution of the two dissolved APIs and then reducing the surrounding pressure to allow the common solvent to sublime. Lyophilisation is preferred in those situations to minimize or eliminated any degradation of the APIs that may otherwise take place due to thermal degradation. Evaporation may be achieved by a variety of available methods, preferably the use of rotary evaporation where the solution of the two dissolved APIs are placed in an evaporation flask that is rotated and heated along with treatment of a pressure drop to facilitate solvent removal and recovery of the two solids APIs. Spray drying is reference to production of a dry powder of the two APIs by rapidly drying via atomization through a spray nozzle to disperse the common solvent into a controlled drop size spray.

It is noted that reference to the feature that the two API's that are dissolved it the common solvent are removed without segregation, is identification of the feature that the two APIs preferably remove themselves from solution in their admixed form. Stated another way, during removal from the common solvent, the two APIs do not phase separate into separate solid regions of API-1 and API-2.

At this point the methodology herein offers at least two options for reducing the particle size of the now recovered mixed APIs. In one embodiment, the recovered APIs may be dry milled to provide particle sizes in the range of 100 nm to 10 microns, more preferably 100 nm to 5.0 microns, and even more preferably to the range of 100 nm to 2.5 microns. Such recovered particles may then be employed to form the final suspension of the particle in a selected liquid carrier for drug administration, which as noted herein, may preferably include a vegetable oil.

In a second embodiment, one can utilize wet milling, where the recovered and mixed APIs are placed directly in a liquid, such as a vegetable oil, which, as discussed more fully herein, is understood an extract from a plant. Such oils may therefore include any one or more of sesame oil, palm oil, soybean oil, safflowerseed oil, rapeseed oil, peanut oil, corn oil, cottonseed oil, grapeseed oil, palm oil, palm kernel oil, coconut oil or olive oil. Preferably, one may utilize cottonseed oil or sesame oil. Wet milling of the mixed APIs is preferably conducted such that the APIs are dispersed in the selected oil by shearing and milling occurs by grinding with beads or balls which can be made of plastic, glass, ceramics or metals. Wet milling will provide particle sizes in the range of 10 nm to 1000 nm. More preferably, wet milling is contemplated to provide particle size in the range of 10 nm to 500 nm, or in the range of 10 nm to 250 nm. As may be appreciated, via the use of wet milling, one will directly provide a suspension containing a relatively low dose API-1 (0.05 mg/mL to 50 mg/mL) and the relatively high dose API-2 (100 mg/mL to 800 mg/mL), which is now discussed more fully below.

As noted above, the final suspension herein is one that can contain 0.1 mg/mL to 10.0 mg/mL of the relatively low dosage API-1. More preferably the range of concentration of such relatively low dosage API-1 can be 0.1 mg/mL to 5.0 mg/mL, or 0.1 mg/mL to 2.5 mg/mL. The final suspension here is also one that preferably contains 20.0 mg/mL to 800.0 mg/mL of the relatively high dosage API-2. More preferably the range of concentration of the relatively high dosage API-2 can be 20.0 mg/mL to 600.0 mg/mL, 20.0 mg/mL to 400.0 mg/mL, or 20.0 mg/mL to 200.0 mg/mL.

The final drug suspension in which the above preferred concentrations of API-1 and API-2 are achieved are suspensions that are preferably formed from vegetable oils, which as noted may be understood as those oils that are extracted from plants or which are synthesized to provide a chemical composition that resembles an extracted oil. For example, the liquids suitable for formation of the final drug suspension herein may include one or more edible oils, such as cottonseed oil, soybean oil and/or sesame oil. Moreover, the liquids herein for formation of the final drug suspension may include organic liquids, such as an organic alcohol, e.g., ethyl alcohol.

In addition, another benefit of the use of vegetable oils herein is that such oil medium was found to provide relatively enhanced stability, over the comparative placement of the API-1 and API-2 in, e.g., an aqueous medium, and in particular, such stability was identified at relatively elevated temperature. Specifically, with attention directed to FIG. 3, a comparison is provided showing the stability of a cottonseed oil (CSO) suspension prepared according to the procedures herein wherein the suspension contains 1.0 mg/ml atropine sulfate and 120 mg/ml 1,1'-methylenebis[4-[(hydroxyimino)methyl]-pyridinium]dimethanesulfonate (MMB4 DMS). More specifically, the stability of MMB4 DMS is identified at time periods of 0, 1, 3, 6, 9 and 12 months, at room temperature, 40° C. and 60° C.

With respect to the various liquids noted above, it is also worth noting that the liquids may be selected such that the liquids themselves are also biocompatible when utilized as the suspension medium for API-1 and API-2. Reference to biocompatible liquid may therefore be understood as a liquid which does not trigger any toxic or injurious effect on the biological system for which it is delivered. Furthermore, it should be appreciated that the above referenced liquids may be combined, e.g., one may utilize a mixture of an organic alcohol and a vegetable oil, which may therefore define a mixture of ethyl alcohol with cottonseed oil, soybean oil and/or sesame oil.

Accordingly, it should be appreciated that when wet milling proceeds in any of these liquid carriers, the need to separately place API-1 and API-2 into the liquid carrier for forming the final suspension may be obviated.

The drug suspensions herein may be particularly suited for treatment of individuals or animals exposed to cholinesterase inhibiting chemicals, such as organophosphates, and accordingly, the drug suspensions herein may serve as organophosphate antidotes. Examples of dosage pairs of the above described relatively low dosage API-1 and relatively high dosage API-2 include, but are not limited to, respectively, a muscarinic antagonist (free base, sulfate salt or hydrobromide salt) which blocks the activity of the muscarinic acetylcholine receptor (e.g. atropine) and an oxime (chemical compounds belonging to the imines of the formula $R_1R_2C=N-OH$) that may reverse the binding of cholinesterase inhibitors with acetylcholinesterase. Other suitable dosage pairs for the relatively low dose API-1 and relatively high dose API-2 include but are not limited to atropine/1,1'-methylenebis[4-hydroxyimino)methyl]-pyridinium (MMB4) salt; atropine/HLo7; atropine/HI6. In addition, it is contemplated herein that the relatively low dosage API-1 may be a mixture of two or more pharmaceutically active ingredients, such as atropine/scopolamine/MMB4 salt; atropine/scopolamine/HI6; atropine/scopolamine/HLo7; atropine/midazolam/MMB4 salt; atropine/midazolam/HI 6; atropine/midazolam/HLo 7. Optionally, in any of these dosage pairs, one may include an excipient.

Figure 2:
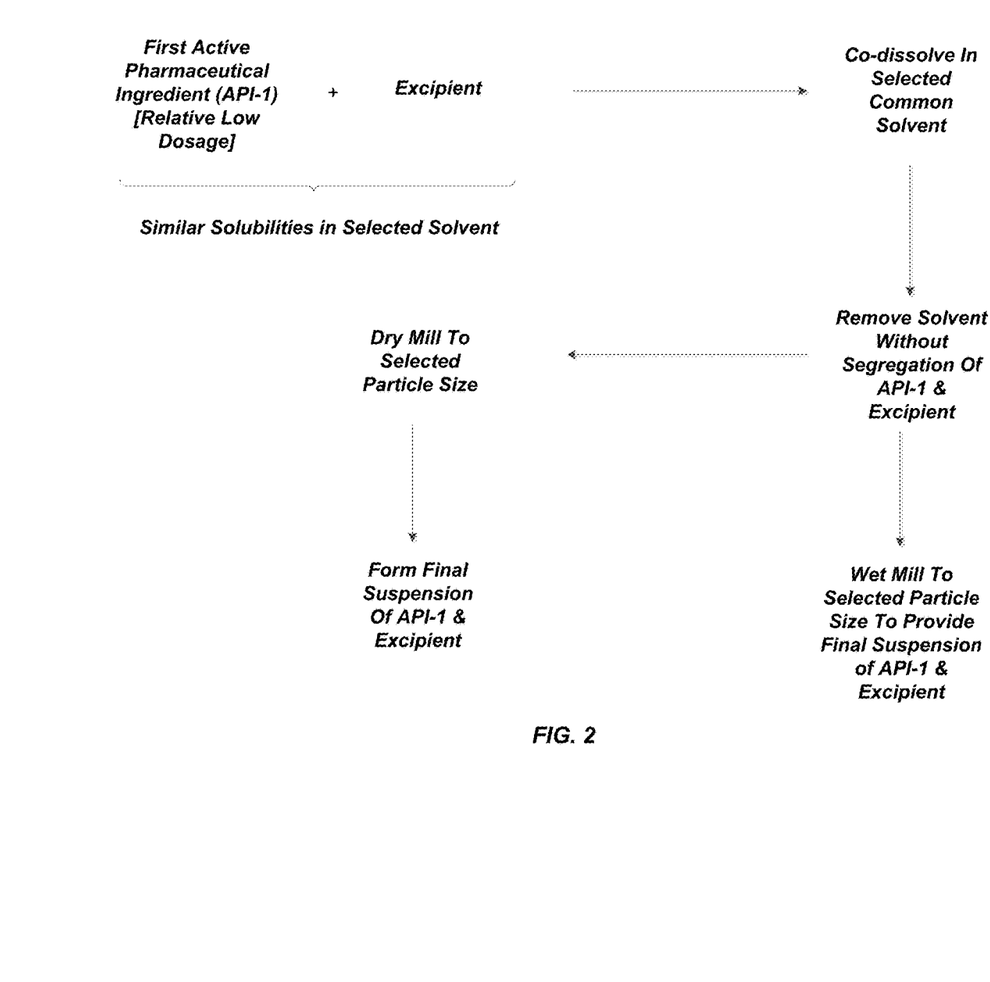
FIG. 2 illustrates the formation of a suspension of an active pharmaceutical ingredient where a first active pharmaceutical ingredient (API-1) is present at relatively low dosage and an excipient is present at a relatively high dosage.
Figure 3:
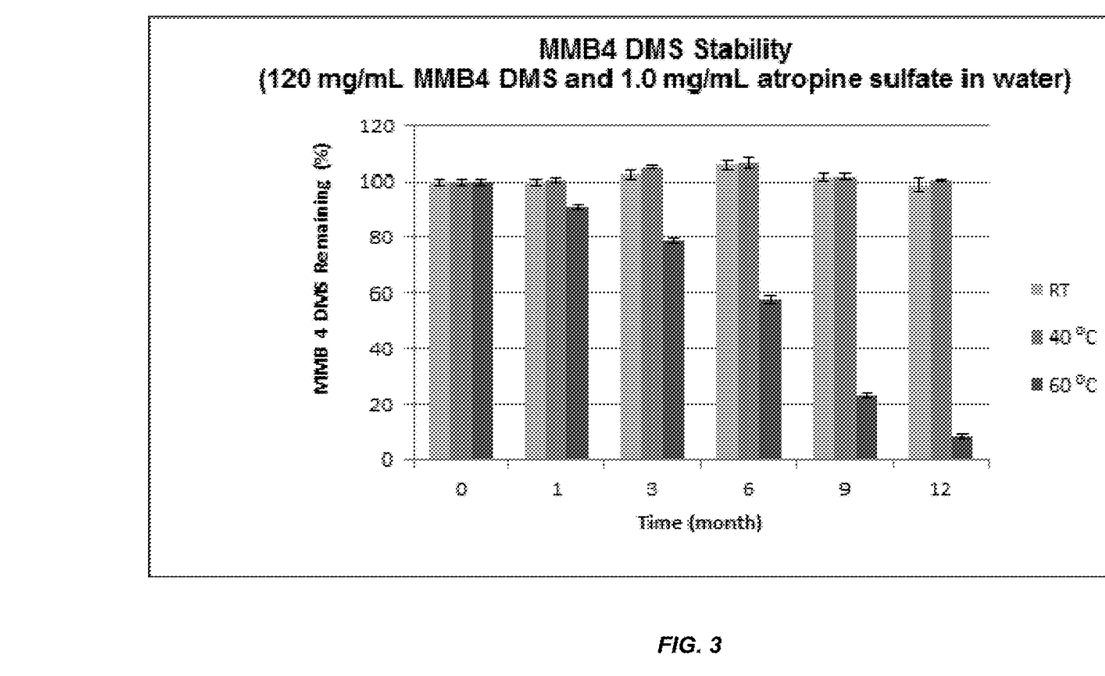
FIG. 3 illustrates a stability study of a suspension of 120 mg/ml of MMB4 DMS (API-2) and 1.0 mg/ml of atropine sulfate (API-1) in water, with regards to the MMB4 DMS component.
Figure 4:
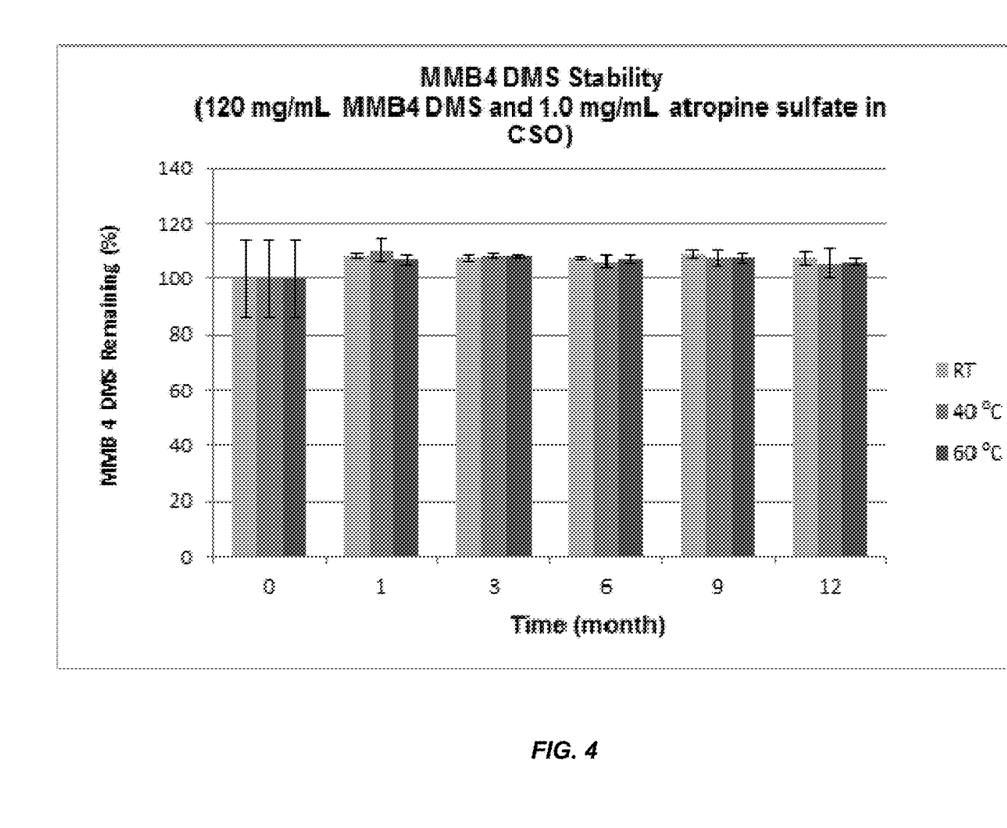
FIG. 4 illustrates a stability study of a suspension of 120 mg/ml of MMB4 DMS (API-2) and 1.0 mg/ml of atropine sulfate (API-1) in cottonseed oil (CSO), with respect to the MMB4 DMS component.
Figure 5:
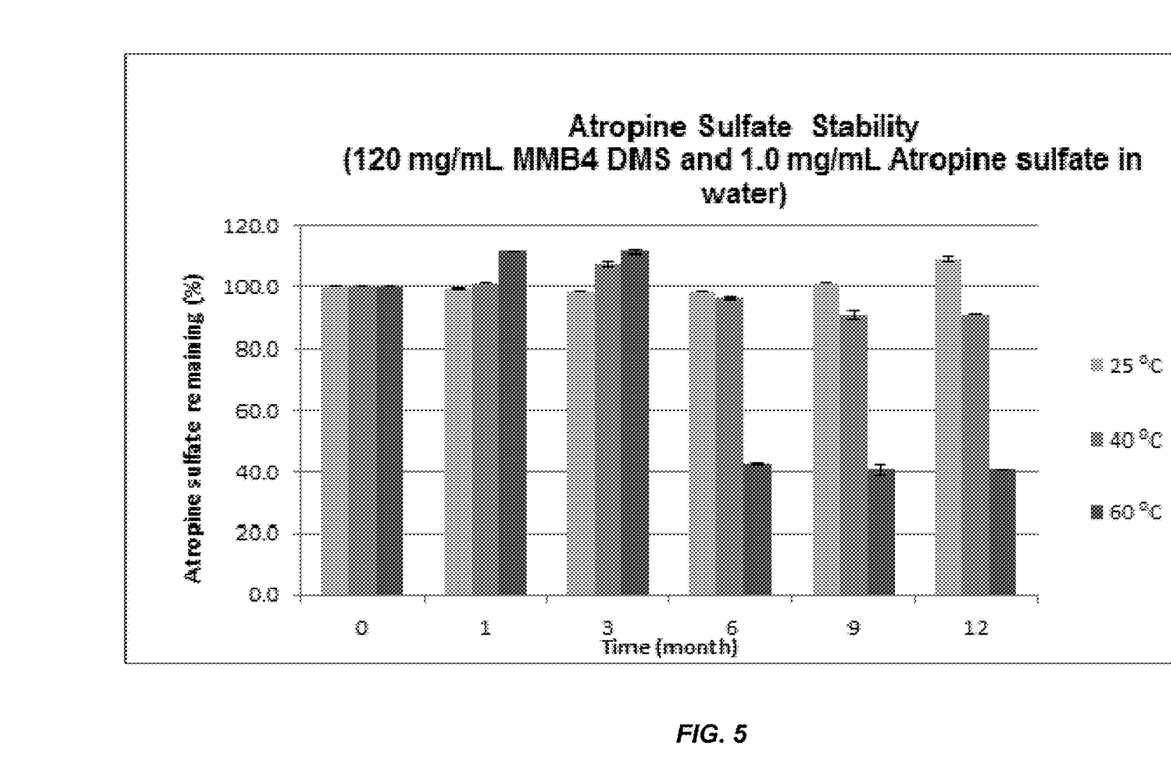
FIG. 5 illustrates a stability study of a suspension of 120 mg/ml of MMB4 DMS (API-2) and 1.0 mg/ml of atropine sulfate (API-1) in water, with regards to the atropine sulfate component.
Figure 6:
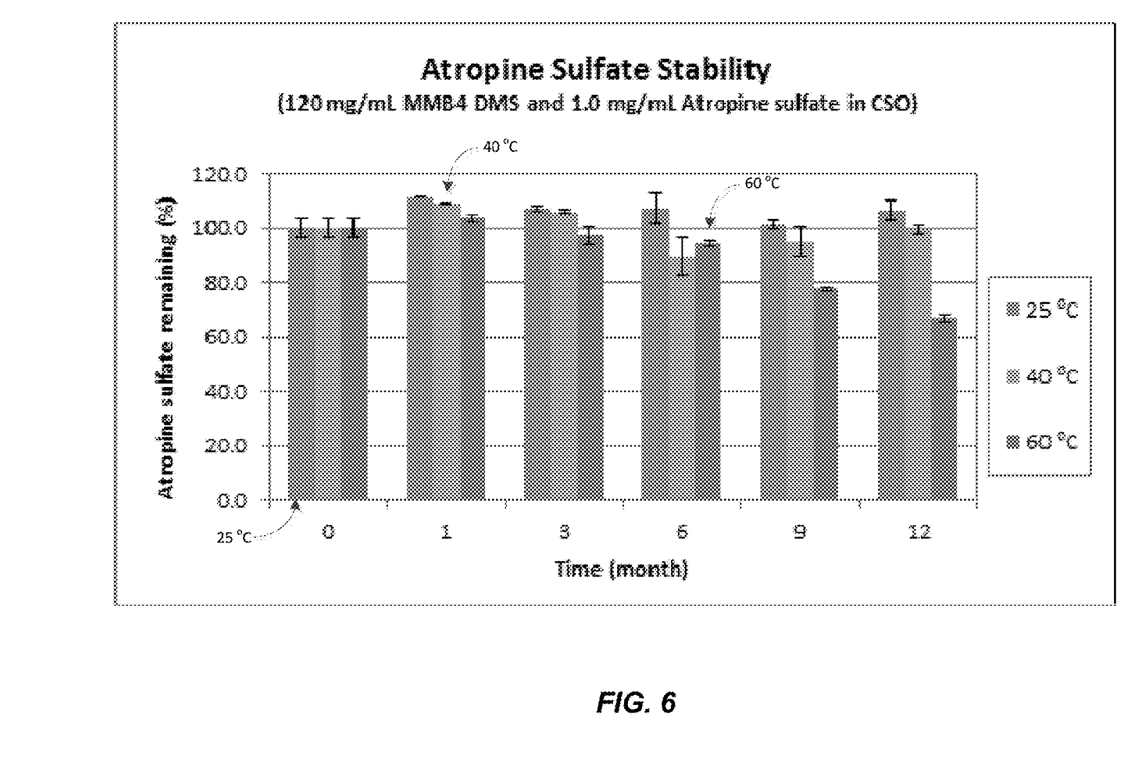
FIG. 6 illustrates a stability study of a suspension of 120 mg/ml of MMB4 DMS (API-2) and 1.0 mg/ml of atropine sulfate (API-1) in cottonseed oil (CSO), with regards to the atropine sulfate component.

Attention is next directed to FIG. 2 which illustrates the present disclosure in related embodiment as applied to the formation of a relatively low dosage API-1 in suspension with an excipient. It will be noticed that this ensuing related embodiment has some similarities to the above, with one difference being that API-2 is replaced by the excipient ingredient, and another difference being the preferred range of concentrations of API-1 and the excipient in the final drug suspension.

Accordingly, a first active pharmaceutical ingredient (API-1) is selected that is targeted for relatively low dosage in the final suspension (e.g. in the range of 0.1 mg/mL to 10.0 mg/mL). An excipient is now also provided in the final suspension such that the excipient will be present at a weight ratio that is 1 to 99 times the weight of the API-1 that is present. By way of example, when API-1 is targeted to be present in the final drug suspension at a level of 0.1 mg/mL, the amount of excipient that is targeted to be present can be up to 9.9 mg/mL. By way of additional example, if the targeted level of API-1 in the final suspension is 10.0 mg/mL, the level of excipient in the suspension can also be 10.0 mg/ml. Accordingly, the level of API-1 and excipient can be preferably varied according to these parameters.

Reference to an excipient is reference to a substance that is included to preferably facilitate injection delivery of the final suspension and/or to facilitate API-1 absorption. Examples include, but are not limited to polyethylene glycol, human serum albumin, lipids, petrolatum (semi-solid mixtures of hydrocarbons with carbon numbers higher than 25), mineral oils (liquid alkanes), biodegradable polymers such as PLGA.

Similar to the above, API-1 and excipient are preferably co-dissolved in a selected common solvent. Preferably, API-1 and the excipient have similar solubility is the selected common solvent. Similar solubility is understood herein to mean that with respect to the weight percent of API-1 and the excipient that co-dissolve in the common solvent, such respective weight percents of dissolution are within plus or minus 10% of one another. By way of example, if API-1 dissolves in the common solvent at a level of 90% by weight, then the excipient will preferably dissolve at the same level of 90% by weight. However, in the broad context of the present disclosure, it should be understood that that the excipient can dissolve at a level at low as 80% by weight to 100% by weight in the selected common solvent medium. In addition, and by way of additional example, if the excipient is such that it dissolves in the selected common solvent at a level of 90% by weight, then API-1 preferably dissolves in the selected common solvent at 90% by weight, or at a level of 80% by weight to 100% by weight.

Accordingly, the common solvent described herein may be any common solvent that provides the indicated solubility requirements. Such solvents may again preferably include water miscible solvents and or water immiscible solvents. The solvents herein may therefore preferably include water, ethanol, isopropanol, acetone, and ethyl acetate.

Continuing, API-1 and the excipient that are dissolved in the common solvent are then next preferably removed from the solvent without segregation. Such removal from the solvent may preferably be achieved by one or more of lyophilisation (freeze drying), evaporation or spray drying. Lyophilisation is reference to the procedure of freezing the solution of the API-1 and the excipient that are dissolved and then reducing the surrounding pressure to allow the common solvent to sublime. Lyophilisation is preferred in those situations to minimize or eliminated any degradation of API-1 that may otherwise take place due to thermal degradation. Evaporation may be achieved by a variety of available methods, preferably the use of rotary evaporation where the solution of API-1 and the excipient are placed in an evaporation flask that is rotated and heated along with treatment of a pressure drop to facilitate solvent removal and recovery of API-1 and the excipient. Spray drying is reference to production of a dry powder of API-1 and the excipient by rapidly drying via atomization through a spray nozzle to disperse the common solvent into a controlled drop size spray.

It is noted that reference to the feature that API-1 and the excipient that are dissolved it the common solvent are removed without segregation, is identification of the feature that API-1 and the excipient preferably remove themselves from solution in their admixed form. Stated another way, during removal from the common solvent, the API-1 and the excipient do not phase separate into separate solid regions of API-1 and the excipient.

At this point the methodology herein again offers at least two options for reducing the particle size of the now recovered API and excipient. In one embodiment, the API-1 and the excipient may be dry milled to provide particle sizes in the range of 100 nm to 10 microns, more preferably 100 nm to 5.0 microns, and even more preferably to the range of 100 nm to 2.5 microns. Such recovered particles may then be employed to form the final suspension of the particle in a selected liquid carrier for drug administration.

In a second embodiment, one can utilize wet milling, where the recovered API-1 and excipient are placed in a liquid, such as a vegetable oil, which is again understood to be an oil extracted from a plant, as described herein. Preferably, one may again utilize cottonseed oil. Wet milling of API-1 and the excipient is again preferably conducted such that API-1 and the excipient are dispersed in the selected oil by shearing and milling occurs by grinding with beads or balls which can be made of plastic, glass, ceramics or metals. Wet milling will again provide particle sizes in the range of 10 nm to 1000 nm. More preferably, wet milling is again contemplated to provide particle sizes in the range of 10 nm to 500 nm, or in the range of 10 nm to 250 nm. As may be appreciated, via the use of wet milling, one will directly provide a suspension containing a relatively low dose API-1 (0.05 mg/mL to 50 mg/mL) and the excipient (100 mg/mL to 800 mg/mL), which is now discussed more fully below.

The final suspension of API-1 and the excipient is one that can contain, as noted, 0.1 mg/mL to 10.0 mg/mL of API-1. More preferably the range of concentration of API-1 can again be 0.1 mg/mL to 10.0 mg/mL, or 0.1 mg/mL to 5.0 mg/mL, or 0.1 mg/mL to 2.5 mg/mL. As noted above, the amount of excipient present is 1 to 99 times the weight of the API-1 that is present in the drug suspension.

In addition, API-1 and the excipient are suspensions that are preferably formed from vegetable oils, edible oils, organic liquids, biocompatible liquids, etc., as noted above in the case of drug suspensions formed from API-1 and API-2 which provide superior stability for the APIs. Accordingly, it may be appreciated that when wet milling proceeds in any of these liquid carriers, the need to separately place API-1 and the excipient into the liquid carrier for forming the final suspension may be obviated.

WORKING EXAMPLES

Example #1

A mixture of scopolamine and MMB4 DMS was obtained after dissolving in water at a ratio of about 1 to 100 (0.10 g and 10.00 g) and subsequent lyophilisation. MMB4 DMS is reference to 1,1'-methylenebis[4-[(hydroxyimino)methyl]-pyridinium]dimethanesulfonate. The mixture was milled in cottonseed oil at about 10.0% by weight solids in the oil to provide a suspension in the oil. Two samples of the suspension, 0.10 g and 1.01 g, were removed and analyzed by high performance liquid chromatography (HPLC) and the results are listed in Table 1 below. It was observed that the amount of scopolamine in the 0.1 g suspension sample was relatively close to the theoretical value demonstrating the homogeneous nature of the solid mixture after the milling process and the ability of accurately delivering a relatively small amount of a given API at a relatively small volume (~0.1 mL).

TABLE 1

| Suspension sample (g) | Scopolamine (mg) | MMB4 DMS (mg) |
|---|---|---|
| 0.10 | 0.104 | 9.4 |
| 1.01 | 1.051 | 100 |

Example #2

A mixture of atropine sulfate and MMB4 DMS similarly prepared and analyzed with similar results as identified in Table 2 below:

TABLE 2

| Suspension sample (g) | Atropine sulfate (mg) | MMB4 DMS (mg) |
|---|---|---|
| 0.10 | 0.114 | 9.5 |
| 1.00 | 1.036 | 90 |

Example #3

A mixture of atropine hydrobromide and MMB4 DMS similarly prepared and analyzed with similar results as identified in Table 3 below:

TABLE 3

| Suspension sample (g) | Atropine hydrobromide (mg) | MMB4 DMS (mg) |
|---|---|---|
| 0.10 | 0.132 | 9.7 |
| 1.00 | 1.268 | 96 |

Stability Evaluations

As noted herein, the APIs indicated relatively enhanced stability when in a vegetable oil suspension. Attention is first directed to FIG. 3, which identifies a stability study of a suspension of 120 mg/ml of MMB4 DMS (API-2) and 1.0 mg/ml of atropine sulfate (API-1) in water, with regards to the MMB4 DMS component. As can be seen, and in particular at 60° C., there is a marked reduction in the remaining concentration of MMB4 DMS over a time period of 12 months. In particular, the available concentration of MMB4 DMS in water medium after 12 months at 60° C. falls to a level of less than 10% of its original concentration. For this stability study, as well as the others now referenced herein, the concentration of the indicated API is carried out by HPLC.

Attention is next directed to FIG. 4 which identifies a stability study of a suspension of 120 mg/ml of MMB4 DMS (API-2) and 1.0 mg/ml of atropine sulfate (API-1) in cottonseed oil (CSO), with respect to the MMB4 DMS component. As can be seen, the available concentration of MMB4 DMS (API-2) remains relatively unchanged after 12 months at 60° C. Accordingly, API-2 is clearly present at a level of 90-100% by weight of its original concentration, after a period of 12 months at 60° C.

Attention is next directed to FIG. 5, which identifies a stability study of a suspension of 120 mg/ml of MMB4 DMS (API-2) and 1.0 mg/ml of atropine sulfate (API-1) in water, with regards to the atropine sulfate component. In particular, the available concentration of atropine sulfate in water medium after 12 months at 60° C. falls to a level of 40.0% of its original concentration.

Attention is next directed to FIG. 6, which identifies a stability study of a suspension of 120 mg/ml of MMB4 DMS (API-2) and 1.0 mg/ml of atropine sulfate (API-1) in cottonseed oil (CSO), with regards to the atropine sulfate component. As can be seen, the available concentration of atropine sulfate (API-1) in cottonseed oil medium after 12 months at 60° C. remains at a level of at least 60.0% of its original concentration. By contrast, as noted above, the available concentration in water had fallen to a much lower level of 40.0%.

As can therefore be appreciated, the vegetable oil suspensions herein are such that with respect to a mixture of API-1 and API-2 in a drug suspension utilizing vegetable oil, both API-1 and API-2 remain at a level of at least 60% of their original concentrations, after a period of up to 12 months at 60° C. More specifically, API-1 remains at a level of at least 60% of its original concentration after a period of up to 12 months at 60° C. in a vegetable oil and API-2 remains at level of at least 90% of its original concentration after a period of up to 12 months at 60° C. in vegetable oil. Such improved stabilities are orders of magnitude improved over corresponding aqueous based formulations.

What is claimed is:

1. A method for forming a drug suspension comprising:
   a) providing a first active pharmaceutical ingredient (API-1);
   b) providing a second active pharmaceutical ingredient (API-2);
   c) co-dissolving said API-1 and API-2 in a common solvent;
   d) removing said solvent and recovering a mixture of API-1 and API-2; and
   e) forming said drug suspension of said mixture of API-1 and API-2 in a liquid carrier, wherein in said drug suspension, API-1 is present at a concentration of 0.1 mg/mL to 10.0 mg/mL and API-2 is present at a concentration of 20.0 mg/mL to 800 mg/mL.

2. The method of claim 1 wherein after removing said solvent and recovering said mixture of API-1 and API-2, said mixture is milled to provide particle sizes in the range of 100 nm to 10 microns.

3. The method of claim 1 wherein after removing said solvent and recovering said mixture of API-1 and API-2, said mixture is wet milled in a liquid carrier to provide particle sizes in the range of 10 nm to 1000 nm.

4. The method of claim 1 wherein said drug suspension is formed in a vegetable oil or organic alcohol.

5. The method of claim 1 wherein API-1 is present in said suspension at a concentration of 0.1 mg/mL to 5.0 mg/mL.

6. The method of claim 1 wherein API-1 is present in said suspension at a concentration of 0.1 mg/mL to 2.5 mg/mL.

7. The method of claim 1 wherein API-2 is present in said suspension at a concentration of 20.0 mg/mL to 600.0 mg/mL.

8. The method of claim 1 wherein API-2 is present in said suspension at a concentration of 20.0 mg/mL to 400.0 mg/mL.

9. The method of claim 1 wherein API-2 is present in said suspension at a concentration of 20.0 mg/mL to 200.0 mg/mL.

10. The method of claim 1 wherein API-1 comprises a muscarinic antagonist.

11. The method of claim 1 wherein API-2 comprises an oxime.

* * * * *